United States Patent [19]

Smith

[11] Patent Number: 4,909,250

[45] Date of Patent: Mar. 20, 1990

[54] IMPLANT SYSTEM FOR ANIMAL IDENTIFICATION

[76] Inventor: Joseph R. Smith, 3372 S. Gadbury Rd., Hartford City, Ind. 47348

[21] Appl. No.: 270,210

[22] Filed: Nov. 14, 1988

[51] Int. Cl.[4] ............................................ A61B 17/00
[52] U.S. Cl. ...................................... 606/117; 40/300
[58] Field of Search ...................... 128/330, 898, 316; 40/300, 637; 426/87, 88; 283/75

[56] References Cited

U.S. PATENT DOCUMENTS

| | | |
|---|---|---|
| 487,304 | 12/1892 | Todd . |
| 881,062 | 3/1908 | Dobyns . |
| 1,257,065 | 2/1918 | Bagby . |
| 1,318,283 | 10/1919 | Johnston . |
| 1,646,921 | 10/1927 | Loose ................................ 426/87 X |
| 1,859,467 | 5/1932 | Rath . |
| 2,705,203 | 3/1955 | Heidrich et al. .................. 426/87 X |
| 3,545,405 | 12/1970 | Jefferts . |
| 4,077,406 | 3/1978 | Sandhage et al. . |
| 4,214,490 | 7/1980 | Chizek . |
| 4,233,964 | 11/1980 | Jefferts et al. . |
| 4,451,254 | 5/1984 | Dinius et al. . |
| 4,672,967 | 6/1987 | Smith . |
| 4,679,559 | 7/1987 | Jefferts . |
| 4,713,315 | 12/1987 | Smith . |

FOREIGN PATENT DOCUMENTS 228022 8/1959 Australia .

OTHER PUBLICATIONS

9 C. F. R. §71.19, "Indentification of Swine in Interstate Commerce", dated Feb. 3, 1988.

Primary Examiner—Michael H. Thaler
Attorney, Agent, or Firm—Charles P. Boukus, Jr.

[57] ABSTRACT

An animal identification system for swine or other livestock employs an identification implant or pellet consisting of food grade material and imprinted with information to identify the source of the animal and its carcass after slaughter. The pellet is implanted under the hide or skin of the animal for purposes of identification. In the case of swine, the identification pellet is located in the fat layer of the shoulder area underneath its hide or skin. The pellet and the imprinted information consist of food grade material which is capable of being dissolved with the fat layer or disintegrated into cracklings in a rendering process. The pellet remains in the carcass after the animal is slaughtered until its removal to permit identification of the source of the animal. If the pellet is not removed, it is either dissolved with the fat of the animal or disintegrated into cracklings in the rendering process. Installation tools are disclosed for implanting the identification pellet in a horizontal or vertical orientation under the hide or skin of the animal.

23 Claims, 3 Drawing Sheets

IMPLANT SYSTEM FOR ANIMAL IDENTIFICATION

FIELD OF INVENTION

The present invention relates to an implant system for animal identification and, more particularly, to an identification system which employs an implant consisting of food grade material and imprinted with information to identify the source of an animal and its carcass after slaughter. Specifically, this invention concerns an identification system for swine or other livestock in which an identification implant consisting of food grade material and imprinted with identifying information is implanted under the hide or skin of the animal for purposes of identification. In the case of swine, the identification implant is located in the fat layer of the shoulder area underneath its hide or skin. The implant and the imprinted information consist of food grade material which is capable of being dissolved with the fat layer in a rendering process or, when required, disintegrated into cracklings by the rendering process. The implant remains in the carcass after the animal is slaughtered until its removal to permit identification of the source of the animal. If the implant is not removed, it is either dissolved with the fat of the animal or disintegrated into cracklings in the rendering process.

BACKGROUND AND PRIOR ART

In the past, various techniques have been proposed and used for purposes of animal identification. The techniques of branding and tattooing of animals are well known. Animal markers such as ear tags and back tags have been used for identification. In addition, it has been proposed to use coded markers or tags embedded under the hide or skin of the animal. See, for example, Todd U.S. Pat. No. 487,304, Dobyns U.S. Pat. No. 881,062, Bagby U.S. Pat. No. 1,257,065, Johnston U.S. Pat. No. 1,318,283 and Jefferts U.S. Pat. No. 3,545,405. In addition, the marking of meats and other food products by insertion of an edible substance is disclosed in Rath U.S. Pat. No. 1,859,467.

For purposes of swine identification, the United States Department of Agriculture has published a proposed rule in the Federal Register, Vol. 53, No. 22, page 3154, dated Feb. 3, 1988, 9 C.F.R. §71.19, requiring all swine to be identified in interstate commerce. The approved means of swine identification include ear tags, back tags, tattoos, ear notching and ear tattoos. These approved means suffer from the following disadvantages.

Back tags have limited life and can be rubbed off easily. Additional labor is required at the slaughtering plant to transfer the identifying information before dehairing of the swine. Also, a secondary identification device is required after dehairing and singeing of the swine. The integrity of identity is subject to errors and omissions due to the potential loss of the back tag from a live animal and the required transfer of information during slaughter. Expensive labor is required at the slaughter plant to transfer information.

Ear tags are costly to apply, labor intensive, and difficult to read at a distance. A secondary identification device is required when the ear tag is removed during slaughter. It is subject to loss during transit and slaughtering of the swine. The integrity of identity is subject to errors and omissions during the transfer of information to a secondary identification device during slaughter. Expensive labor is required at the slaughter plant to transfer the information.

Tattoos exhibit problems with legibility when improperly applied to the swine. The identifying information can be lost during trimming/or skinning operations. A tattoo is subject to duplication, does not lend itself to sequential numbering, and is messy to apply.

Ear notching and ear tattooing require registration in a national breed register which is not possible for cross-bred animals. This requirement only applies to breeding stock, not market hogs. Some purebred breeds are difficult to recognize as a carcass. Ear notching is subject to duplication and subject to error because of notches improperly positioned in the ear. Ear notching and ear tattooing are costly because of the registration fees required. Also, older animals tend to develop torn ears, reducing the legibility of ear notches and ear tattoos.

In view of the difficulties discussed above, an identification system for swine or other livestock which is easily applied and capable of accurate identification of both live animals and carcasses is desirable. In addition, it is desirable that the identification system be biologically compatible with the swine or other livestock and easily disposable after the slaughter of the animal.

SUMMARY OF INVENTION

The present invention achieves an identification system for animals such as swine or other livestock which overcomes the disadvantages of the prior art by utilizing a biologically compatible implant or pellet suitable for implantation under the hide or skin to identify the source of the live animal and its carcass after slaughter. The pellet is imprinted with information to identify the source of the animal. The pellet and its imprinted information consist of food grade material which is biologically compatible with the live animal and capable of being dissolved with the fat of the animal in a rendering process after slaughter or, when required, disintegrated into cracklings by the rendering process. The identifying information can be printed on the pellet in ink which also consists of food grade material. A preferred embodiment of the pellet is an elongated, flat-faced cylinder with the identifying information printed on the cylindrical surface of the pellet.

This invention also contemplates a device for implanting the identification pellet in the fat layer beneath the hide or skin of the animal. The implanting device may be designed to insert the identification pellet in a horizontal or vertical orientation under the hide or skin of the animal. In addition, the implanting device can be furnished in a kit together with a plurality of identification pellets bearing the same identifying information.

In accordance with the invention, a method of identifying an animal consists of implanting an identification pellet comprised of food grade material beneath the hide or skin of the animal, with the pellet being imprinted with information for purposes of identification of the animal. The identifying information can be printed on the pellet in ink consisting of food grade material. The food grade material of the pellet is capable of being dissolved with the fat layer of the animal in a rendering process or, when required, disintegrated into cracklings by the rendering process. The pellet remains implanted in the carcass of the animal after it is slaughtered until removal of the pellet to identify the source of the animal. Preferably, the pellet is a small, elongated cylinder with coded information printed on its cylindrical surface which is implanted vertically or horizontally under the hide or skin of the animal.

The present invention provides an animal identification system, particularly suitable for swine, in which the biologically compatible, implanted pellet serves to accurately identify the source of the live animal and its carcass after slaughter. Since the pellet consists of food grade material, it is readily disposable in a rendering process after the slaughter of the animal.

The identification system of the present invention has the advantages that the identification pellet is easily and quickly applied, economical, permanent and tamperproof. The information on the pellet is easily readable. The identification pellet is easily detected in an animal carcass and easily removed from the carcass when required for identification. The pellet constitutes a food grade device which is compatible with further processing and presents no danger in the food chain. Thus, removal of the pellet is not required on passed or approved carcasses. No additional labor is required to transfer the identifying information from the pellet at the time of slaughter. Thus, possible errors or omissions are avoided. The pellet is acceptable for dehairing and skinning operations. Duplications of the identifying information for carcass origins can be avoided. The original purchaser of the pellet can be easily traced through the manufacturer of the pellet.

DETAILED DESCRIPTION OF PREFERRED EMBODIMENT

Figure 1:
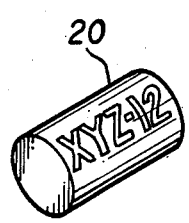
FIG. 1 is a perspective view of a biologically compatible animal identification implant or pellet.

Referring to FIG. 1, a preferred embodiment of the animal identification implant of this invention comprises a cylindrically shaped, flat-faced cylindrical pellet 20 which is suitable for implantation under the hide or skin of an animal, e.g., a swine or other livestock. Pellet 20 is imprinted with identifying information, e.g., the alphanumeric legend "XYZ-12", for purposes of identification of the animal. In actual use, the identifying information can be the owner's name, tax identification number, farm name, Social Security number, or a sequence of alphanumeric characters assigned by the U.S.D.A. or requested by an individual for his exclusive use. The pellet can be implanted in domestic food animals such as swine, cattle, sheep and goats.

In accordance with the invention, the identification pellet 20 is fabricated from material intended to be biologically compatible with the animal in which it is implanted. A biologically compatible material within the meaning of this invention is a material which does not interfere with the ability of the animal to function normally and which does not cause infections or other veterinary problems in the animal. For example, the pellet 20 is fabricated entirely of food grade material approved by the United States Food and Drug Administration. Preferably, the food grade material is selected to be capable of being dissolved with the fat of the animal in a rendering process or, when required, disintegrated into cracklings by the rendering process. Cracklings are the crisp bits which remain of pork fat after the rendering process is completed.

In a preferred embodiment, the identifying information is printed on pellet 20 in ink consisting of food grade material. Pellet 20 is made cylindrical in shape and the information is printed on the cylindrical surface of the pellet. For example, the pellet may consist of an elongated, flat-faced cylinder which is approximately 5/32 inch in diameter and 7/16 inch in length.

The identifying information can be applied to the pellets by an ink jet printer using ink with color additives approved by the FDA and supplied by Imaje Ink Jet Printing, Suite 100, 5500 Highlands Parkway, Smyrna, Ga., 30082. The types of ink approved by the FDA are the following:

ED 1112 B2 Blue Ink
ED 1112 B1 Red Ink
ED 1112 B1 Black Ink
ED 1122 I1 White Ink
ED 1122 B1 White Ink Sample pellets were made as follows. The pellets were compressed in 4 mm (5/32 inch) diameter dies using flat-faced punches. The target length was 0.210 to 0.245 inch. The target hardness was at least 20 Strong Cobb. The desired result was a pellet which could be implanted under the hide or skin of an animal and not break down in the live animal, but which would break up or disintegrate in the rendering process. A formula containing white wax was found to be suitable for these purposes.

In the following example, the ingredients are listed by weight percent.

EXAMPLE I (Formula BC20)

| | |
|---|---|
| Calcium sulfate | 77.69% |
| White Wax (white beeswax) | 19.84% |
| Magnesium stearate | 0.80% |
| Polyvinylpyrollidone | 1.66% |
| FD & C Yellow #6 (sunset yellow) | 0.01% |
| Total | 100.00% |

In Example I, the calcium sulfate was used as a diluent or filler for the pellets. White wax was used as the ingredient which enabled the pellet to break up or dissolve in the rendering process. Magnesium stearate served as a lubricant, and polyvinylpyrollidone provided a binder. The ingredient identified as FD&C Yellow #6 was a coloring agent.

As mentioned above, it is desired that the identification pellet consist of food grade material which is capable of being dissolved with the fat of the animal or disintegrated into cracklings in a rendering process after the animal is slaughtered. Typically, an animal rendering process is conducted at temperatures in the range of 60° C. to 80° C. In Example I, the melting temperature of the white wax was 65° C. Thus, in a rendering process conducted at temperatures at or above the melting point of the white wax, the pellet is capable of being dissolved with the fat of the animal or being disintegrated into cracklings in the rendering process.

To achieve the desired characteristics, it is contemplated that a preferred embodiment of the pellet should include between 17% and 23% white wax by weight. Alternatively, stearic acid or carnauba wax may be used in place of the white wax in the formulation of the pellet. In addition, it is contemplated that various combinations of white wax, stearic acid and carnauba wax may be employed in the pellet formula.

Figure 2:
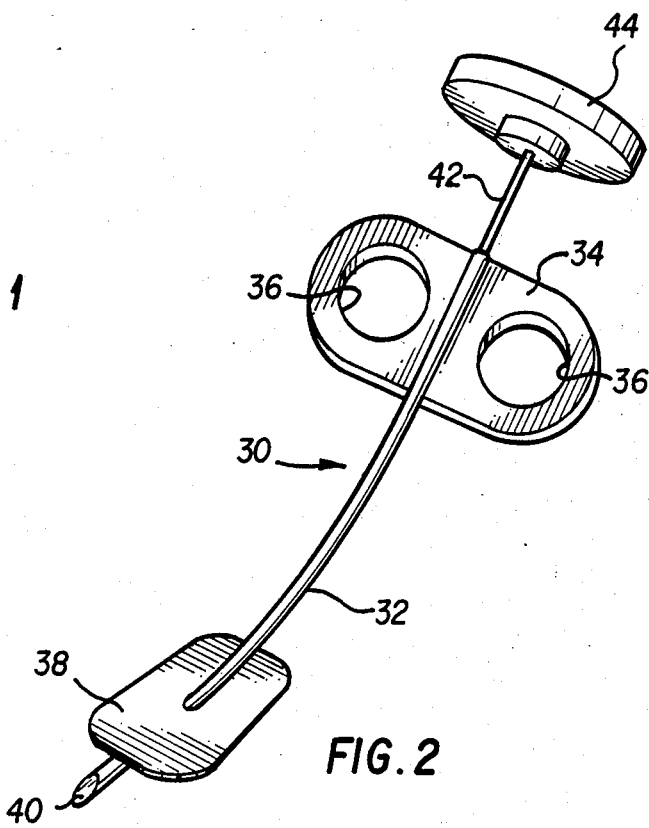
FIG. 2 is a perspective view of a manual tool for installation of the identification pellet.
Figure 3:
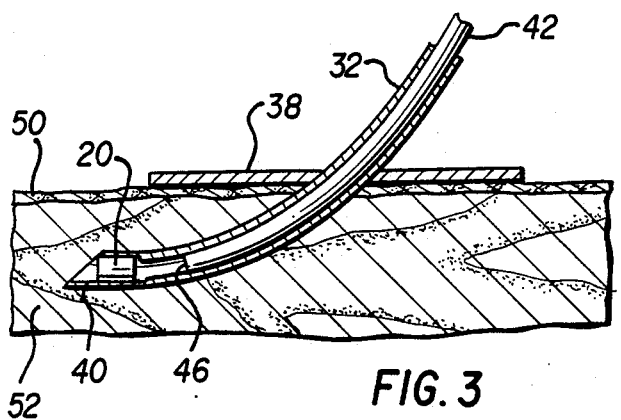
FIG. 3 is a section view showing the installation tool with its tip inserted into the fat layer beneath the hide or skin of an animal.
Figure 4:
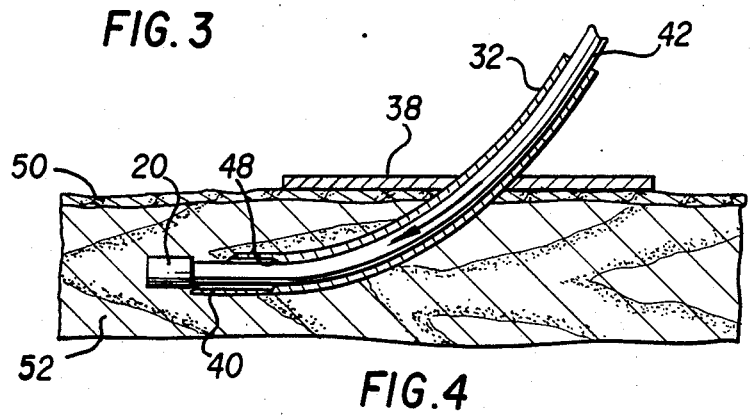
FIG. 4 is a section view illustrating the actuation of the installation tool to implant the identification pellet in the fat layer of the animal.

Referring to FIG. 2, a manually operated installation tool, generally 30, designed for pellet implantation in a horizontal orientation, comprises an elongated, curved needle-like tube 32 secured at its upper end to a finger grip 34 having a pair of finger openings 36 at opposite sides. The lower end of tube 32 extends through a flat support plate 38 and terminates at a tapered, sharpened point 40 which facilitates insertion of the tool into the animal. As shown in FIG. 3, tip 40 of needle-like tube 32 is oriented horizontally, i.e., parallel to support plate 38. An elongated, flexible plunger 42 is slidably received within needle-like tube 32. An actuator knob 44 is attached to the upper end of plunger 42. The lower end of plunger 42 terminates at a flat face 46 (FIG. 3) which engages pellet 20 when plunger 42 is actuated. Needle-like tube 32 includes a recessed offset 48 (FIG. 4) adjacent to its pointed tip 40 to receive the pellet 20.

Preferably, in the construction of installation tool 30, the actuator knob 44 is made of plastic and the needle-like tube 32 is made of stainless steel. The finger grip 34 and support plate 38 are made of polished steel, and the plunger 42 is made of flexible steel.

To accomplish the implantation, an identification pellet 20 is loaded into the tip 40 of needle-like tube 32 and positioned against its recessed offset 48. Then, as shown in FIG. 3, the pointed tip 40 is inserted through the hide or skin 50 of the animal into the layer of fat 52 beneath the hide or skin 50. Tip 40 is pushed into the layer of fat 52 until plate 38 rests on the hide or skin 50 of the animal. Then, referring to FIGS. 2 and 4, plunger 42 is actuated by pushing actuator knob 44 downward to drive identification pellet 20 from tip 40 of the installation tool 30 into the layer of fat 52 of the animal. Subsequently, by pulling on finger grip 34, the needle-like tube 32 is withdrawn from the animal. As a result, pellet 20 is implanted horizontally in the layer of fat 52 beneath the hide or skin 50 of the animal.

Figure 5:
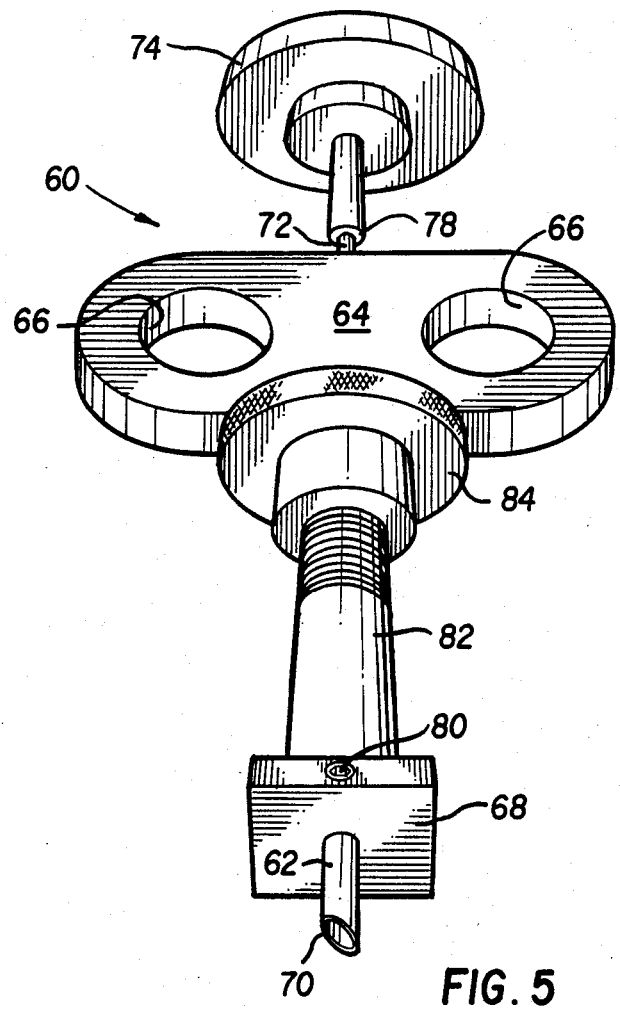
FIG. 5 is a perspective view of an alternative tool for installation of the identification pellet.
Figure 6:
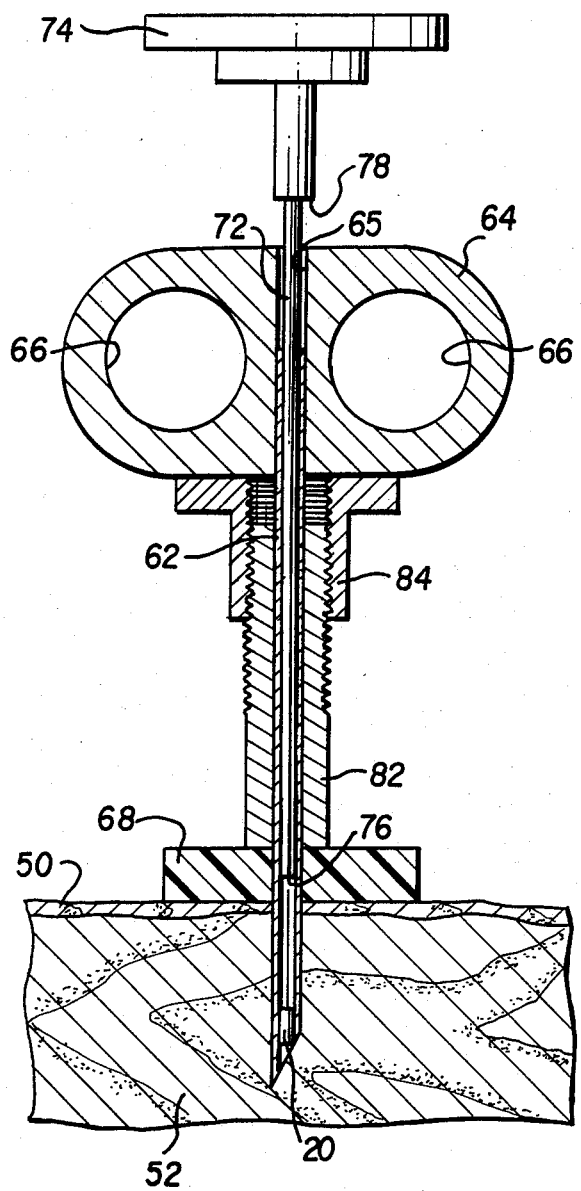
FIG. 6 is a vertical section view illustrating the insertion of the installation tool of FIG. 5.

Referring to FIG. 5, an alternative manually operated installation tool, generally 60, designed for pellet implantation in a vertical orientation, comprises an elongated, needle-like tube 62 secured at its upper end to a finger grip 64 having a pair of finger openings 66 at opposite sides. Needle-like tube 62 is secured by soldering or welding in a vertical bore 65 (FIG. 6) in finger grip 64 with its upper end extending about halfway into the vertical bore 65. The lower end of needle-like tube 62 extends through a depth adjustment block 68 and terminates at a tapered, sharpened point 70 which facilitates insertion of the tool into the animal. As shown in FIG. 6, tip 70 of needle-like tube 62 is oriented vertically, i.e., perpendicular to adjustment block 68. An elongated plunger 72 is slidably received within needle-like tube 62. An actuator knob 74 is attached to the upper end of plunger 72. The lower end of plunger 72 terminates at a flat face 76 (FIG. 6) which engages pellet 20 when plunger 72 is actuated. The upper end of plunger 72 is enlarged to provide an offset 78 which engages the upper end of needle-like tube 62 when the actuator knob 74 is depressed to limit the downward movement of plunger 72.

To adjust the depth of implantation of pellet 20 by tool 60, depth adjustment block 68 is slidably mounted on needle-like tube 62. A set screw 80 is mounted on the adjustment block 68 to secure the block 68 to needle-like tube 62 at various heights relative to its sharpened tip 70. A sleeve 82 is slidably mounted on needle-like tube 62 between finger grip 64 and adjustment block 68. The upper end of sleeve 82 is threadably connected to an adjustment collar 84. To adjust the depth of penetration of needle-like tube 62 into the animal, set screw 80 is loosened and adjustment collar 84 is rotated clockwise or counterclockwise to adjust sleeve 82 and adjustment block 68 to a desired length. Next, the adjustment block 68 is moved upward into contact with the lower end of sleeve 82 until collar 84 engages finger grip 64. Then, set screw 80 is tightened to secure the adjustment block 68 to the needle-like tube 62 to set its sharpened tip 70 to the desired depth of penetration.

Preferably, in the construction of installation tool 60, the depth adjustment block 68 and actuator knob 74 are made of plastic and the needle-like tube 62 is made of stainless steel. The finger grip 64 and plunger 72 are made of polished steel. Also, the sleeve 82 and adjustment collar 84 are made of polished steel.

Figure 7:
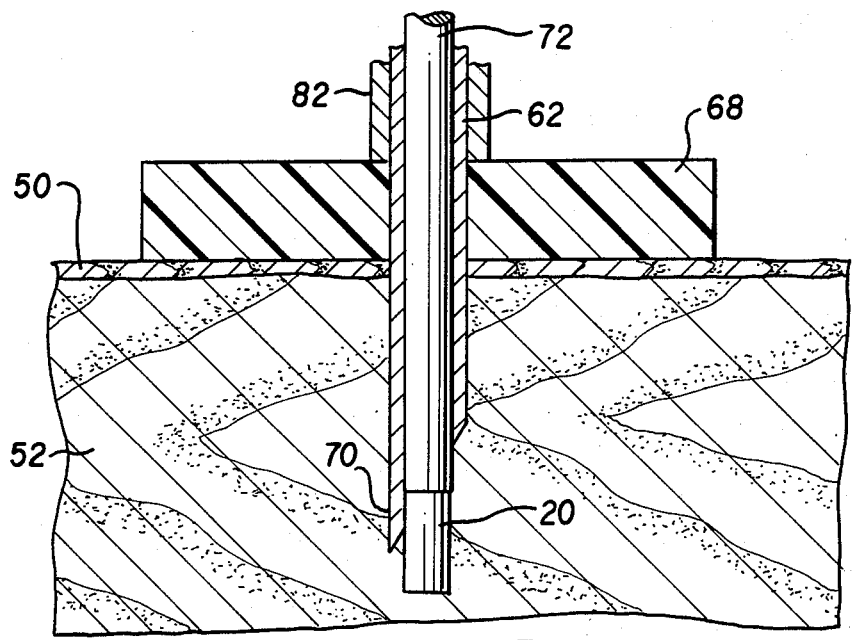
FIG. 7 is an enlarged section view illustrating the actuation of the installation tool of FIG. 5.

To accomplish the implantation, an identification pellet 20 is loaded into the tip 70 of needle-like tube 62. Then, as shown in FIG. 6, the pointed tip 70 is inserted through the hide or skin 50 of the animal into the layer of fat 52 beneath the hide or skin 50. Tip 70 is pushed into the layer of fat 52 until block 68 rests on the hide or skin 50 of the animal. Next, referring to FIGS. 6 and 7, plunger 72 is actuated by pushing actuator knob 74 downward until offset 78 engages the upper end of needle-like tube 62 to drive identification pellet 20 from tip 70 of the installation tool 60 into the layer of fat 52 of the animal. Subsequently, by pulling on finger grip 64, the needle-like tube 62 is withdrawn from the animal. As a result, pellet 20 is implanted vertically in the layer of fat 52 beneath the hide or skin 50 of the animal.

Alternatively, to accomplish the implantation with installation tool 60, the plunger 72 is completely withdrawn from needle-like tube 62 before the tool is inserted into the animal. Then, the pointed tip 70 is inserted through the hide or skin 50 of the animal into the layer of fat 52 beneath the hide or skin 50. Tip 70 is pushed into the layer of fat 52 until block 68 rests on the hide or skin 50 of the animal. Next, an identification pellet 20 is dropped into the upper end of needle-like tube 62 through vertical bore 65. Then, plunger 72 is inserted into the upper end of needle-like tube 62 and actuated by pushing actuator knob 74 downward until offset 78 engages the upper end of needle-like tube 62 to drive identification pellet 20 from tip 70 of the installation tool 60 into the layer of fat 52 of the animal. Subsequently, by pulling on finger grip 64, the needle-like tube 62 is withdrawn from the animal leaving pellet 20 implanted vertically in the layer of fat 52 beneath the hide or skin 50 of the animal.

Preferably, for swine, the identification pellet 20 is implanted in the layer of fat beneath its hide or skin in the shoulder area of the swine. For example, a single identification pellet is implanted subcutaneously at a depth of about $\frac{3}{8}$ inch in the outer fat layer of the swine and approximately 3 to 4 inches on either side of the backbone and posterior of the shoulder blade of the swine.

To minimize the requirements for aseptic techniques and reduce the potential for site infection, the implanting of the identification pellet in the swine should be performed within 72 hours prior to slaughter. However, it is also contemplated that the identification can be implanted in the swine at an early age, e.g., 9 to 10 weeks, and that the pellet can remain implanted until the slaughter of the swine, typically at an age of 6 to 7 months.

The alphanumeric codes imprinted on the pellet are recorded at the time of implanting and are included in the bill of sale when the animal is sold for slaughter. The implant remains in the host but is readily detectable by slaughter plant and regulatory personnel at the subcutaneous injection site. The identification pellet is easily removed from the carcass by making a single cut along the implant site and manually expressing the pellet. The code is compared with the daily invoices to determine the origin of the carcass. For carcasses not requiring identification, the implant is removed with the trimmed fat and the pellet dissolves with the fat during the normal rendering process or, when required, disintegrates into cracklings.

It is contemplated that the pellets bearing the identifying information for a particular source of swine or other livestock will be furnished together with one of the installation devices shown in FIGS. 2 and 5 or with some other suitable tool. For example, the installation tool may include a cartridge for receiving a plurality of pellets and for feeding the pellets sequentially to the installation tool.

It is also contemplated that the identification system of the present invention may be employed for the purpose of owner identification of domestic pets and for tracking the migration and habitat of wildlife. For domestic pets and wildlife, the identification pellet can be implanted under the skin of the animal at its front leg flanks or in its wing cavities. In addition, the identification system can be employed in humans for such purposes as identification of infants, military personnel and hospital patients, and for identification of persons with major health concerns requiring special treatment in case of emergency. For humans, the identification pellet can be implanted under the skin in the arm pit area.

The invention in its broader aspects is not limited to the specific details shown and described, and modifications may be made in the animal identification system disclosed above without departing from the principles of the present invention.

I claim:

1. An identification implant for an animal, comprising:
    a biologically compatible pellet for implantation under the hide or skin of the animal;
    said pellet being imprinted with information for purposes of identification of said animal; and
    said pellet and said imprinted information being comprised of food grade material, said food grade material being adapted not to break down in the live animal.
2. The implant of claim 1, wherein:
    said food grade material is capable of being dissolved with the fat of said animal or disintegrated into cracklings in a rendering process after said animal is slaughtered.
3. The implant of claim 2, wherein:
    said food grade material includes an amount of white wax, stearic acid or carnauba wax sufficient to enable said pellet to dissolve or disintegrate into cracklings in the rendering process.
4. The implant of claim 1, wherein:
    said information is printed on said pellet in ink which consists of food grade material.
5. The implant of claim 1, wherein:
    said pellet is cylindrical in shape and said information is printed on the cylindrical surface of said pellet.
6. A method of animal identification consisting of implanting an identification pellet comprised of food grade material beneath the hide or skin of a live animal, said pellet being imprinted with information for purposes of identification of the source of said animal and its carcass after slaughter.
7. The method of claim 6, wherein:
    said information is printed on said pellet in ink which consists of food grade material.
8. The method of claim 6, wherein:
    said food grade material of said pellet is capable of being dissolved with said fat layer of said animal or disintegrated into cracklings in a rendering process after said animal is slaughtered.
9. The method of claim 8, which includes:
    removing said pellet from the carcass of said animal after it is slaughtered to identify the source of said animal.
10. The method of claim 8, wherein:
    said pellet is implanted in a horizontal orientation under the hide or skin of said animal.
11. The method of claim 8, wherein:
    said pellet is implanted in a vertical orientation under the hide or skin of said animal.
12. The method of claim 6, wherein:
    said pellet is a small, elongated cylinder and coded information is printed on the cylindrical surface of said pellet to identify the source of the animal.
13. The method of claim 6, wherein:
    said food grade material of said pellet is adapted not to break down in the live animal.
14. A method of swine identification consisting of implanting an identification pellet comprised of food grade material in the fat layer beneath the hide or skin of a live swine, said pellet being imprinted with coded information for purposes of identification of the source of said swine and its carcass after slaughter.
15. The method of claim 14, wherein:
    said coded information is printed on said pellet in ink which consists of food grade material.
16. The method of claim 14, wherein:
    said food grade material of said pellet is capable of being dissolved with said fat layer of said swine or disintegrated into cracklings in a rendering process after said swine is slaughtered.
17. The method of claim 14, which includes:
    removing said pellet from the carcass of said swine after it is slaughtered to identify the source of said swine.
18. The method of claim 14, wherein:
    said pellet is implanted subcutaneously at a depth of about ⅜ inch in the outer fat layer of said swine and approximately 3 to 4 inches on either side of the backbone and posterior of the shoulder blade of said swine.
19. The method of claim 14, wherein:
    said food grade material of said pellet is adapted not to break down in the live animal.
20. An identification system for an animal, comprising:

a biologically compatible pellet for implantation under the hide or skin of the animal;

said pellet being imprinted with information for purposes of identification of said animal;

said pellet and said imprinted information being comprised of food grade material; and a device for implanting said pellet under the hide or skin of the animal.

21. The system of claim 20, wherein:

said device is adapted to implant said pellet in the fat layer beneath the hide or skin of said animal.

22. The system of claim 21, wherein:

said food grade material of said pellet and said imprinted information is capable of being dissolved with said fat layer of said animal or disintegrated into cracklings in a rendering process after said animal is slaughtered.

23. The method of claim 20, wherein:

said food grade material of said pellet is adapted not to break down in the live animal.

* * * * *